(12) United States Patent
Keller et al.

(10) Patent No.: US 12,280,339 B2
(45) Date of Patent: Apr. 22, 2025

(54) HOLLOW FIBRE MEMBRANE WITH IMPROVED SEPARATING EFFICIENCY, AND PRODUCTION OF A HOLLOW FIBRE MEMBRANE WITH IMPROVED SEPARATING EFFICIENCY

(71) Applicant: FRESENIUS MEDICAL CARE DEUTSCHLAND GMBH, Bad Homburg (DE)

(72) Inventors: Torsten Keller, St. Wendel (DE); Michael Paul, Lebach (DE); Roland Sander, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 17/895,085

(22) Filed: Aug. 25, 2022

(65) Prior Publication Data

US 2022/0410080 A1    Dec. 29, 2022

Related U.S. Application Data

(62) Division of application No. 16/467,057, filed as application No. PCT/EP2017/081955 on Dec. 8, 2017, now Pat. No. 11,478,759.

(30) Foreign Application Priority Data

Dec. 9, 2016    (DE) .................... 10 2016 224 627.5

(51) Int. Cl.
*B01D 65/02*    (2006.01)
*B01D 69/08*    (2006.01)
(Continued)

(52) U.S. Cl.
CPC ......... *B01D 69/088* (2013.01); *B01D 65/022* (2013.01); *B01D 71/441* (2022.08);
(Continued)

(58) Field of Classification Search
None
See application file for complete search history.

(56) References Cited

U.S. PATENT DOCUMENTS

| 4,840,769 A | 6/1989 | Nejigaki et al. |
| 4,919,810 A | 4/1990 | Itoh et al. |

(Continued)

FOREIGN PATENT DOCUMENTS

| CA | 1294745 C | 1/1992 |
| DE | 3936785 C1 | 3/1991 |

(Continued)

OTHER PUBLICATIONS

Hulko, Michael, et al. "Requirements and pitfalls of dialyzer sieving coefficients comparisons." Artificial Organs 42.12 (2018): 1164-1173. (Year: 2018).*

(Continued)

*Primary Examiner* — Bradley R Spies
*Assistant Examiner* — Jeannie McDermott
(74) *Attorney, Agent, or Firm* — Kilyk & Bowersox, P.L.L.C.

(57) ABSTRACT

The invention relates to a method for manufacturing a hollow fiber membrane bundle from a plurality of polysulfone and PVP-based hollow fiber membranes which encompasses the providing of a spinning solution comprising a polysulfone-based material, in particular polysulfone, a vinylpyrrolidone-based polymer, in particular polyvinylpyrrolidone, an aprotic solvent, in particular dimethylacetamide, providing a coagulant liquid comprising water and an aprotic solvent, in particular dimethylacetamide, co- (Continued)

Nominal pores size distribution for Ex. 2 and Ex. 3 comparative membrane extruding the spinning solution and the coagulant liquid through a concentric annular spinneret into a hollow strand, whereby the cavity of the strand is filled with coagulant liquid, conducting the strand through a precipitation gap, introducing the strand into a precipitating bath comprised substantially of water so as to obtain a hollow fiber membrane, conducting the hollow fiber membranes through at least one rinsing bath and drying the hollow fiber membrane obtained, arranging the resulting hollow fiber membranes into a hollow fiber membrane bundle, and treating the hollow fiber membrane bundle with water vapor.

16 Claims, 7 Drawing Sheets

(51) Int. Cl.
  *B01D 71/44* (2006.01)
  *B01D 71/68* (2006.01)
  *B01D 71/62* (2006.01)

(52) U.S. Cl.
  CPC ............. *B01D 71/62* (2013.01); *B01D 71/68* (2013.01); *B01D 2323/081* (2022.08); *B01D 2323/12* (2013.01); *B01D 2325/0283* (2022.08); *B01D 2325/26* (2013.01)

(56) References Cited

U.S. PATENT DOCUMENTS

| | | | | |
|---|---|---|---|---|
| 4,935,141 | A * | 6/1990 | Buck | B01D 69/12 264/44 |
| 5,147,613 | A | 9/1992 | Heilmann et al. | |
| 5,376,274 | A | 12/1994 | Muller et al. | |
| 5,407,581 | A * | 4/1995 | Onodera | B01J 20/3248 210/508 |
| 5,851,394 | A * | 12/1998 | Shibata | B01D 69/08 210/500.21 |
| 6,013,182 | A * | 1/2000 | Emi | B01D 69/02 210/321.71 |
| 6,478,960 | B1 * | 11/2002 | Saruhashi | B01D 67/0088 210/500.24 |
| 2006/0144782 | A1 | 7/2006 | Buck | |
| 2006/0205309 | A1 * | 9/2006 | Mabuchi | B01D 71/68 442/338 |
| 2007/0163949 | A1 | 7/2007 | Wechs et al. | |
| 2007/0199891 | A1 * | 8/2007 | Mabuchi | D01D 5/24 264/41 |
| 2008/0237127 | A1 * | 10/2008 | Okafuji | A61M 1/16 210/321.61 |
| 2009/0238967 | A1 | 9/2009 | Helff et al. | |
| 2010/0012577 | A1 | 1/2010 | Krause et al. | |
| 2010/0190965 | A1 | 7/2010 | Yamaguchi et al. | |
| 2010/0224553 | A1 | 9/2010 | Ansorge et al. | |
| 2012/0305472 | A1 | 12/2012 | Yokota et al. | |
| 2013/0338297 | A1 | 12/2013 | Ford et al. | |
| 2015/0283517 | A1 | 10/2015 | Takahashi et al. | |
| 2015/0293094 | A1 | 10/2015 | Ladisch et al. | |
| 2016/0207009 | A1 | 7/2016 | Menda et al. | |
| 2016/0228314 | A1 | 8/2016 | Tamai et al. | |
| 2017/0165616 | A1 | 6/2017 | Boschetti-De-Fierro et al. | |
| 2019/0381462 | A1 | 12/2019 | Keller et al. | |

FOREIGN PATENT DOCUMENTS

| | | |
|---|---|---|
| EP | 0841086 A1 | 5/1998 |
| EP | 3088069 A1 | 11/2016 |
| JP | S61242604 A | 10/1986 |
| JP | H08506519 A * | 7/1996 |
| JP | H09220445 A | 8/1997 |
| JP | 2006116383 A | 5/2006 |
| JP | 2007003213 A | 1/2007 |
| WO | 2008156124 A | 12/2008 |
| WO | 2013034611 A1 | 3/2013 |

OTHER PUBLICATIONS

International Search Report and Written Opinion issued in corresponding International Patent Application No. PCT/EP2017/081955 (with English translation of International Search Report) dated Jun. 7, 2018 (24 pages).

Office Action issued in corresponding Korean Patent Application 10-2019-7016297 dated May 10, 2022 (7 Pages).

International Preliminary Report on Patentability issued in corresponding International Patent Application No. PCT/EP2017/081955 dated Jun. 11, 2019 (14 pages).

Office Action issued in corresponding Australian Patent Application 2017373828 dated Apr. 4, 2023 (5 Pages).

Simone et al., "Preparation of hollow fibre membranes from PVDF/PVP blends and their application in VMD," Journal of Membrane Science, 2010, vol. 364, pp. 219-232.

Mulder, M., "Basic Principles of Membrane Technology—2nd edition," Kluwer Academic Publishers, 1996, pp. 71-88.

* cited by examiner

Test set up for zeta potential determination

Local ultrafiltration coefficients of hollow fiber membrane filter cross section Hollow fiber membrane filter sterilization method - Step 1

Hollow fiber membrane filter sterilization method - Step 2

Hollow fiber membrane filter sterilization method - Step 3

Hollow fiber membrane filter sterilization method - Step 4

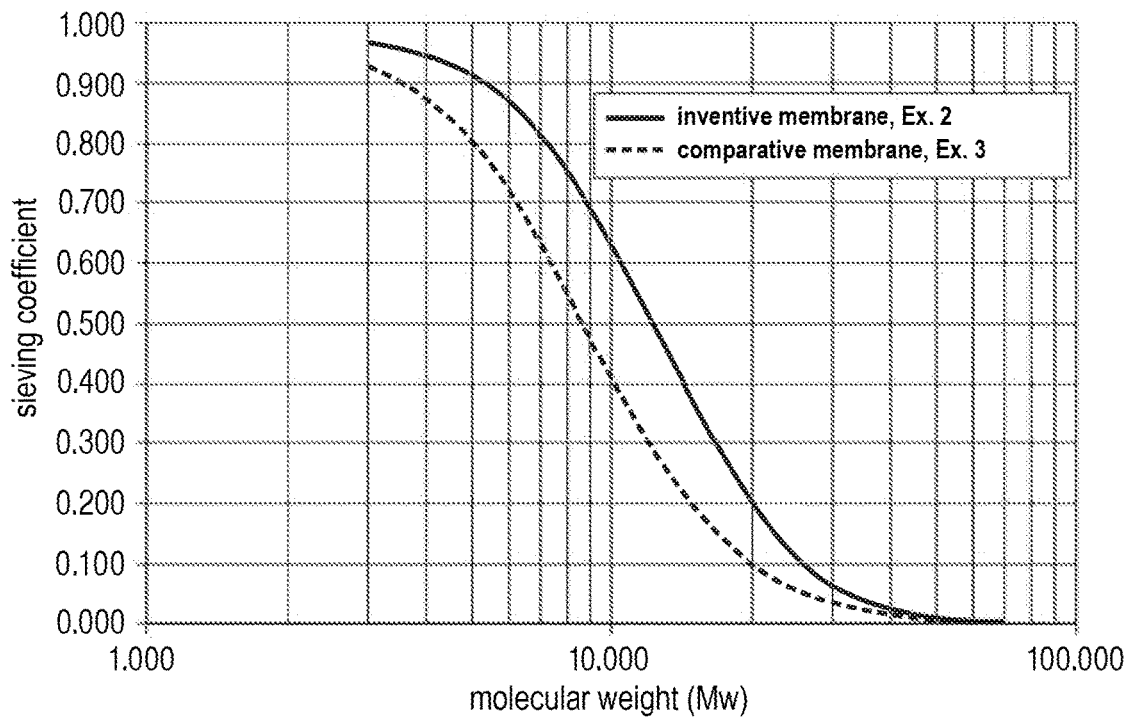
Fig. 7: Dextran sieving coefficient for Ex. 2 membrane and Ex. 3 comparative membrane
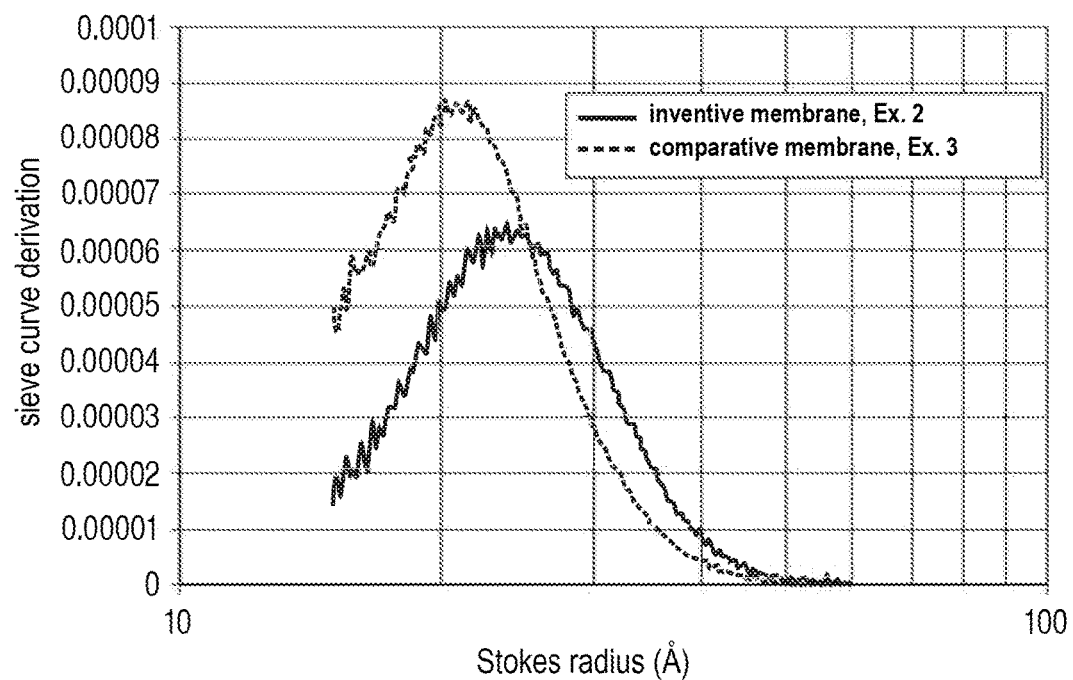
Fig. 8: Nominal pores size distribution for Ex. 2 and Ex. 3 comparative membrane

HOLLOW FIBRE MEMBRANE WITH IMPROVED SEPARATING EFFICIENCY, AND PRODUCTION OF A HOLLOW FIBRE MEMBRANE WITH IMPROVED SEPARATING EFFICIENCY

This application is a divisional of U.S. patent application Ser. No. 16/467,057 filed Jun. 6, 2019, which is a National Stage Application of PCT/EP2017/081955, filed Dec. 8, 2017, which claims priority to German Patent Application No. 10 2016 224 627.5, filed Dec. 9, 2016.

SUBJECT MATTER OF THE INVENTION

The invention relates to hollow fiber membranes comprising a polysulfone and polyvinylpyrrolidone-based membrane material having improved separation properties, in particular improved capability in separating substances in the mid-molecular weight range and improved selectivity with respect to separating substances in the high mid-molecular weight range.

The invention further relates to a method for manufacturing hollow fiber membranes having a polysulfone and polyvinylpyrrolidone-based membrane material.

The invention moreover relates to a hollow fiber membrane filter comprising hollow fiber membranes having homogeneous permeation properties.

In particular, the invention relates to a method of sterilizing hollow fiber membranes of a polysulfone and polyvinylpyrrolidone-based membrane material.

BACKGROUND OF THE INVENTION

Hollow fiber membranes are widely used in the filtration of liquids. In particular, hollow fiber membranes are used in medical applications for purifying water and blood during dialysis treatments of patients with kidney disease. The corresponding hollow fiber membranes are formed into hollow fiber membrane bundles within filter modules. Filter modules of this type for hemopurification are produced on a mass scale.

The hollow fiber membranes used for hemopurification are commonly composed of polysulfone (PSU) and polyvinylpyrrolidone (PVP), since these materials have proven preferentially hemocompatible and are thus preferential from a medical perspective in the treatment of blood, particularly in hemodialysis. The basic principles of producing hollow fiber membranes as well as their manufacture are described in the prior art:

Marcel Mulder; Principles of Membrane Technology; Kluwer Academic Publisher 1996; Chapter III, Preparation of synthetic membranes
EP 0 168 783
WO 2007/128440

According to these methods described in the prior art, a spinning solution is prepared which comprises a polysulfone-based hydrophobic material and a vinylpyrrolidone-based hydrophilic polymer, particularly polyvinylpyrrolidone, and one or more solvents and any additives which might be needed. Polar aprotic solvents can serve as the solvents, particularly dimethylacetamide, N-methylpyrrolidone, dimethyl formamide or dimethyl sulfoxide. The spinning solution can likewise comprise small quantities of additives, e.g. polar protic solvents, e.g. water, at low percentages.

The spin mass is extruded through a circular spinneret. The spinneret thereby has an inner bore through which a precipitant is channeled and co-extruded together with the spin mass. The spin mass is extruded through an annular gap surrounding the inner bore into a hollow fiber, into the lumen of which the precipitant is introduced. The spinning fiber is then introduced into a precipitating bath containing another precipitant such that a membrane structure forms into a hollow fiber membrane by way of phase inversion and precipitation. Water or mixtures of protic and aprotic solvents, in particular water and dimethylacetamide, N-methylpyrrolidone, dimethyl formamide or dimethyl sulfoxide, serve as the precipitant. The resulting hollow fiber membrane is thereafter passed through rinsing baths and dried and wound onto a coiler. The hollow fiber membranes can be removed from the coiler in the form of hollow fiber bundles. To construct hollow fiber membrane filters, such hollow fiber membrane bundles are placed into a housing, preferably a cylindrical housing. The ends of the hollow fiber membrane bundle are embedded into a casting compound and the open ends of the hollow fibers are exposed. The casting compound forms a sealing region between the interior of the hollow fiber membranes, the housing and the area surrounding the hollow fiber membranes. A first chamber is thereby formed in the finished hollow fiber membrane filter which encompasses the inlet and outlet regions of the ends of the hollow fiber membrane bundle as well as the interior of the hollow fiber membranes. A second chamber accordingly forms in the area within the space between the hollow fiber membranes and between the housing wall and the hollow fiber membranes. Fluid ports on the housing of the hollow fiber membrane filter allow the liquids and fluids to be conducted in and out of the first and/or the second chamber of the hollow fiber membrane filter.

At least one fluid port thereby forms an inlet to the first chamber of the hollow fiber membrane filter. At least one fluid port forms an inlet to the second chamber of the hollow fiber membrane filter. Further inlets to the first or second chamber are provided as necessary depending on the intended application of the hollow fiber membrane filter to be produced. Hollow fiber membrane filters which are intended for the extracorporeal treatment of blood usually have a first and a second fluid port to the first chamber of the filter module and a first and a second fluid port to the second chamber of the filter module. Fluids, particularly liquids or gases, can thus be fed to or drained from a chamber of the hollow fiber membrane filter via the first port depending on the direction of flow, or fed to or drained from a chamber of the hollow fiber membrane filter via the second port according to the direction of flow.

For hollow fiber membrane filters intended for medical purposes, particularly those intended for treating the blood of patients with kidney disease, one or more rinsing and sterilization steps usually follows in the hollow fiber membrane and filter production process in order to purify and sterilize the hollow fiber membranes for medical use.

Corresponding methods are known in the prior art in which the hollow fiber membranes in hollow fiber membrane filters undergo rinsing and sterilization steps. In particular, heat sterilization of hollow fiber membrane filters with air, water or water vapor constitutes a known sterilization procedure for hollow fiber membranes and hollow fiber membrane filters. Heat sterilization is to be understood as a sterilization with fluids (e.g. air, water, water vapor or mixtures thereof) above a temperature of 100° C. Heat sterilization with predominantly pure water vapor is also called steam sterilization. Such a method for sterilizing dialyzers is described in DE 39 36 785 C1. According to the method described in DE 39 36 785 C1, the dialyzers are subjected to a rinsing process followed by a sterilizing process. In the sterilization process, the dialyzers are flushed with water or water vapor heated to more than 121° C.

Further methods known in the prior art for sterilizing filter modules include vacuum steam sterilization, sterilization using sterilizing gases, e.g. ethylene oxide, and irradiation with ionizing or radical-forming radiation, e.g. electron radiation or gamma radiation.

It has been shown that the thermocycling in vacuum steam sterilization adversely affects the stability of the hollow fiber membranes to be sterilized. In vacuum steam sterilization, the procedural steps of vaporization and evacuation of the autoclave alternate. With each evacuation step, the temperature of the autoclave and the hollow fiber membrane filter inevitably drops far below that during the vaporization step. The hollow fiber membrane filter is thereby subject to constantly changing material expansion. Disadvantageous material stresses can thus occur in the vacuum steam sterilization process. This places correspondingly complex demands on the material selection as well as the processing and design of the hollow fiber membrane filters.

Sterilization with ionizing radiation such as e.g. gamma or electron radiation is coupled with high equipment costs and results in lengthy additional treatment time.

Sterilization with ethylene oxide likewise requires an enormous system expenditure due to the ethylene oxide's toxicity. In addition, a long phase is required after sterilization for the necessary total elimination of the ethylene oxide.

Compared to the other cited sterilization methods, the heat sterilization realized with flushing and sterilization steps using water and/or water vapor as realized pursuant to DE 39 36 785 C1 has proven technically superior in terms of the equipment and the procedure. In particular, this water/water vapor heat sterilization has proven superior to the irradiation or gassing sterilization methods with respect to the blood compatibility of the sterilized hollow fiber membranes.

It has however also been shown that for polysulfone membranes which contain polyvinylpyrrolidone, the steam sterilization method cited in DE 39 36 785 C1 can adversely affect the clearance of the hollow fiber membranes. It is assumed that the flushing process during the sterilization process mobilizes the PVP present on the hollow fiber membrane. The capillary forces of the membrane pores attract and constrict the mobilized PVP into the pores of the hollow fiber membrane, or block the pore cross section. This has the applicative consequence of a smaller pore cross section for filtration. The deposit of PVP in the pores accordingly diminishes the permeation properties of the hollow fiber membranes.

Appropriately adapting the production of the hollow fiber membranes attempts to counteract the diminished permeation properties of the hollow fiber membranes caused by the sterilization procedure. Doing so results in also disadvantageously broadening the hollow fiber membrane's pore size distribution. The pore size distribution of hollow fiber membranes thereby has a direct effect on the hollow fiber membrane's selectivity.

The method of DE 39 36 785 C1 further shows that due to the PVP present within a hollow fiber membrane filter, the hollow fiber membranes can cling together in the dialyzer in the previous water/water vapor sterilization process methods. This was not disadvantageous with respect to the required sterility. However, it was seen that the sterilization process on such agglomerated hollow fiber membranes yielded inhomogeneous performance properties to the hollow fiber membranes within a hollow fiber membrane filter. It was in particular found that areas within a hollow fiber membrane filter in which hollow fiber membranes were clustered during sterilization exhibited diminished permeation properties compared to the areas exhibiting no agglomeration of hollow fiber membranes.

In consideration of this aspect, there was cause to further develop the rinsing and sterilization processes of a steam sterilization method for hollow fiber membrane filters so as to be able to prevent an agglomeration of hollow fiber membranes within a hollow fiber membrane module and to additionally be able to prevent the constricting or blocking of pores by mobilized and deposited PVP and at the same time maintain the high sterility and blood compatibility of the hollow fiber membranes and the hollow fiber membrane filter.

A substantial characterizing property of hollow fiber membranes in this respect is the clearance. Clearance is a measure of the separation capability of a hollow fiber membrane and indicates the effort needed to be able to remove noxious metabolites during hemopurification by treatment of hollow fiber membranes. Methods for determining the clearance of hollow fiber membranes are known in the prior art. Reference is made in this respect to the DIN/EN/ISO 8637:2014 standard. The clearance of a hollow fiber membrane is thereby determined pursuant to the standard by constructing a test filter from the membrane which is adapted to the corresponding circumstances.

In the development of hollow fiber membranes for extracorporeal blood treatment, the aim is to develop hollow fiber membranes having the highest possible separation capability so as to provide effective types of therapy for extracorporeal blood treatment.

The separation capability of a substance is particularly influenced by the porosity and the average pore size of a membrane. The porosity indicates the ratio of pore volume in a membrane. When a membrane exhibits a higher pore volume than a comparative membrane, a higher material transport is observed across the membrane wall contingent upon the average pore size.

Particularly for therapies in the chronic extracorporeal treatment of blood, a high separation capability of plasma proteins in the mid-molecular range is desirable. Concurrently, however, a high retention of plasma proteins in the high molecular weight range, such as e.g. albumin, is necessary. At the same time, high hollow fiber membrane hemocompatibility is also sought in the extracorporeal treatment of blood.

OBJECT OF THE INVENTION

It has been shown that previous methods in the production of steam-sterilized polysulfone and polyvinylpyrrolidone-based hollow fiber membranes suffer from a limited separation capability and selectivity due to the sterilization procedure, particularly a limited separation capability for mid-molecular weight range plasma proteins at a predetermined albumin retention.

In a first aspect of the invention, the task is thus that of providing a hollow fiber membrane having high separation capability (clearance) in the mid-molecular weight range and high retention in the high molecular weight range, whereby the hollow fiber membrane at the same time exhibits a high blood compatibility as provided by heat sterilization with water or water vapor.

In a second aspect of the invention, the task is further that of providing a hollow fiber membrane filter exhibiting homogeneous performance properties with respect to the hollow fiber membranes within a hollow fiber membrane filter.

In a third aspect of the invention, the task is that of providing an improved method for producing hollow fiber membranes which comprises water or water vapor-based rinsing and/or sterilization steps without diminishing the separation capability of the hollow fiber membranes during the rinsing and/or sterilization steps.

In a fourth aspect of the invention, the task is moreover that of providing a water or water vapor-based rinsing and/or a sterilization method for hollow fiber membrane filters which does not adversely affect the performance properties of the hollow fiber membranes.

SUMMARY OF THE INVENTION

In a first aspect of the invention, it was surprisingly found that the above-cited task is solved by a hollow fiber membrane having the features as described herein including preferential implementations of the invention according to the first aspect.

In a second aspect of the invention, it was shown that the above-cited task is solved by a hollow fiber membrane filter having the features as further described herein.

In a third aspect of the invention, it was seen that the above-cited task is solved by a novel method for producing hollow fiber membranes having the features as further described herein.

In a fourth aspect of the invention, it was shown that the above-cited task is solved by a method for purifying a hollow fiber membrane filter pursuant to the features as further described herein.

BRIEF DESCRIPTION OF THE DRAWINGS

FIG. 7 is a graph showing dextran sieving coefficients for the membrane of Example 2 and the membrane of Comparative Example 3.

FIG. 8 is a graph showing nominal pore size distributions for the membrane of Example 2 and the membrane of Comparative Example 3.

DETAILED DESCRIPTION OF THE INVENTION

Figure 1:
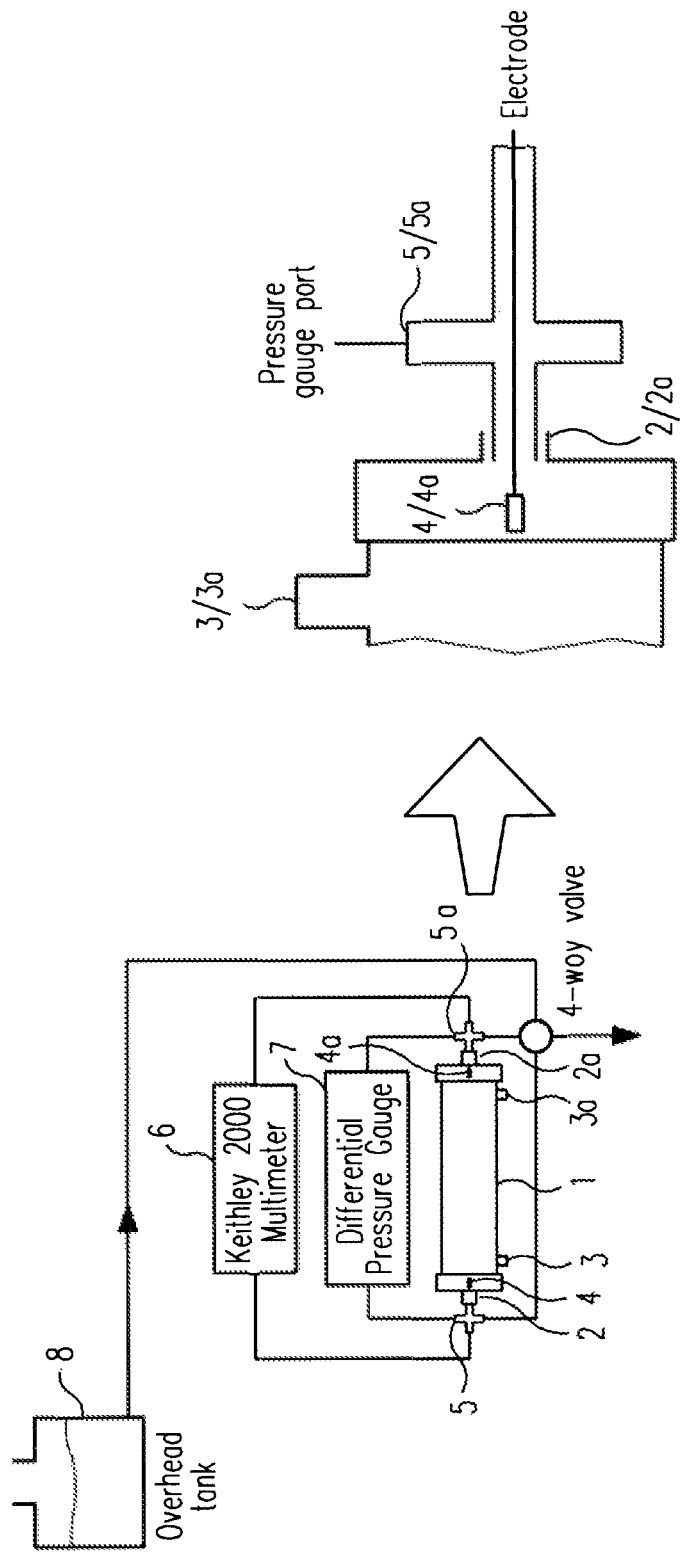
FIG. 1 shows an apparatus/test set-up for zeta potential determination of a fiber.

Surprisingly shown in a first aspect of the invention is that a hollow fiber membrane having improved separation capability in the mid-molecular weight range can be provided when the hollow fiber membrane comprises at least one polysulfone-based material and at least one vinylpyrrolidone-based polymer and the hollow fiber membrane has a porosity of 77.5% to 82% and a sieving coefficient for dextran at the molecular weight of 10,000 g/mol of 0.42 to 0.75.

A hollow fiber membrane according to the first aspect of the invention is characterized by high permeability in the mid-molecular weight range. It has particularly been further shown that such hollow fiber membranes prove to be hemocompatible since they can be produced from polysulfone and polyvinylpyrrolidone-based polymers and can be purified following a rinsing process and sterilized in a sterilization process.

In accordance with the first aspect of the invention, the material of the hollow fiber membranes is polysulfone-based. To be understood by the present definition of a polysulfone-based polymer is a polymer exhibiting a sulfone group in the polymer main or side chain. The term polysulfone (PSU) is to be understood in the context of the present application as a generic term for all polymers containing sulfone groups. Typical representatives of polysulfone-based materials are polysulfone (PSU), polyether sulfone (PES), polyphenylsulfone and copolymers containing sulfone groups. Although not listed here, further representatives of polysulfone polymers are known in the prior art and are suitable for producing blood treatment membranes as defined by the invention. Polysulfone materials have proven superior over other materials in the manufacture of blood treatment membranes since they are steam sterilizable and exhibit good hemocompatibility properties.

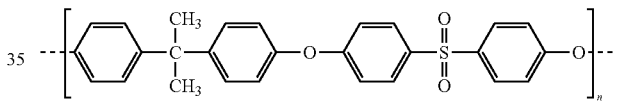

Polysulfone (PSU)

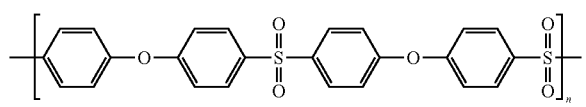

Polyether Sulfone (PES)

To be understood by a vinylpyrrolidone-based polymer is a polymer produced using the vinylpyrrolidone monomer or derivatives thereof. Particularly polyvinylpyrrolidone (PVP) is well-suited in the context of the present invention for the production of inventive hollow fiber membranes. PVP is a water-soluble polymer which is used as an adjuvant in the production of polysulfone-based hollow fiber membranes. PVP moreover effects an improvement in the hemocompatibility of polysulfone hollow fiber membranes as it hydrophilizes the hydrophobic polysulfone material and thereby improves wettability to blood.

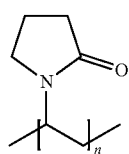

Polyvinylpyrrolidone (PVP)

Hemocompatibility refers to tolerance to human blood, particularly as regards blood which contacts polysulfone materials not undergoing any negative reactions which could be harmful to the health of patients over the course of a blood treatment. These can for example refer to blood clotting phenomena or a proclivity to damage blood cells (cytotoxicity). Using PSU/PVP polymers has proven superior in terms of blood compatibility compared to other blood-contact materials in hollow fiber membranes.

Particularly polysulfone and polyvinylpyrrolidone-based hollow fiber membrane materials are characterized by their zeta potential value. Zeta potential is a measure of the electrical charges that can be found on surfaces of substrates. Particularly on blood treatment membranes, this surface charge is associated with harmful reactions. Polysulfone and polyvinylpyrrolidone-based membranes exhibit different zeta potential values depending on the method used to produce the hollow fiber membrane.

The porosity of a membrane indicates the pore volume ratio of a membrane material. With hollow fiber membranes, only the ratio of pore volume on the membrane wall is hereby considered. The lumen of a hollow fiber membrane is not taken into account when calculating porosity. Porosity represents a measure of the permeability of a hollow fiber membrane to fluids and is thus also a measure of the separation capability of the membrane relative to molecules of a certain size. Particularly in conjunction with the sieving coefficient of a molecule at a specific molecular weight, porosity is regarded as a measure of the separation capability of the membrane for said molecule. In the present case, it has been found that a hollow fiber membrane having a sieving coefficient of 0.42 to 0.75 for a dextran molecule at the molecular weight of 10,000 g/mol, in conjunction with a porosity of 77.5% to 82% of the hollow fiber membrane to the average molecular weight range of plasma proteins, is characteristic of high permeability or clearance respectively in the average molecular weight range and a high separation selectivity with respect to high-molecular plasma proteins, albumin in particular, for a hollow fiber membrane. Preferential is a hollow fiber membrane which is characterized by having substantially no macrovoids or dendritic cavities. Dendritic cavities are understood as macrovoids having finger-like elongations. Macrovoids are described in the cited literature ("Mulder"). Examples of the formation of dendritic cavities can additionally be found in WO2004/056460 A1 FIG. 1, WO2013/034611 A1 FIGS. 1, 2 and 3 or WO2015/056460 A1 FIG. 5. Membranes without dendritic cavities or macrovoids exhibit higher mechanical stability. Further preferential is a membrane characterized by a wall thickness of 35 μm or less and substantially no macrovoids or dendritic cavities. At such slight wall thicknesses, it is particularly important to ensure good mechanical stability.

The sieving coefficient indicates the proportion of a considered substance which is capable of permeating through the membrane wall during a filtration process. In particular applicable to a hollow fiber membrane having a low sieving coefficient for high molecular molecules is that they are for the most part held back by the membrane wall during filtration and only a small percentage is able to permeate through the pores of the hollow fiber membrane. Efforts are made in the production of blood-treatment hollow fiber membranes to create a pore structure to the hollow fiber membrane which enables a high retention of high molecular plasma proteins such as e.g. albumin and which is characterized by a correspondingly low sieving coefficient for albumin of 0.01, preferentially 0.005, particularly preferentially 0.001. On the other hand, a high sieving coefficient for molecules of low molecular weight implies that virtually all of these molecules are able to permeate the membrane wall of the hollow fiber membrane through the pore structure.

The pore size distribution of a membrane according to the invention is thereby to be structured so as to yield a sieving coefficient of 0.42 to 0.75 as described for a dextran at a molecular weight of 10,000 g/mol and the sieving coefficient for albumin assumes a value as described of less than 0.1.

In a further implementation according to the first aspect of the invention, the inventive hollow fiber membrane is characterized by a zeta potential value of from −3 mV to −10 mV. It was particularly apparent that harmful reactions with blood cells only occur to a lesser extent within this range of values.

In a further implementation of the first aspect of the invention, it was seen that the selectivity of the hollow fiber membrane could be improved when the hollow fiber membrane has a porosity of 78% to 81%, particularly a porosity from 79% to 80.5%.

In a further implementation according to the first aspect of the invention, it was seen that the selectivity of the hollow fiber membrane could be further improved when the hollow fiber membrane has a sieving coefficient for a dextran molecule at the molecular weight of 10,000 g/mol of 0.45 to 0.75, preferentially 0.55 to 0.7, particularly a sieving coefficient of 0.6 to 0.7.

In a further implementation of the first aspect of the invention, it was seen that the selectivity of the hollow fiber membranes could be improved when the hollow fiber membrane has an albumin sieving coefficient of less than 0.005, in particular less than 0.001.

In a further embodiment of the first aspect of the invention, it was seen that the blood compatibility of the hollow fiber membrane could be improved by the hollow fiber membrane having a zeta potential of −4 mV to −8 mV, particularly a zeta potential of −6 mV to −8 mV.

In a further embodiment of the first aspect of the invention, it was seen that the blood compatibility of the hollow fiber membrane could be improved when the hollow fiber membrane has a PVP content of 2.5% to 5%.

In a further implementation of the first aspect of the invention, it was seen that the inventive membrane has a maximum of nominal pore size distribution in the range of from 22 to 26 Å (Å=angstrom=100 ppm). In particular shown was that a maximum of the nominal pore size distribution in this molecular weight range can achieve desired high separation of the mid-molecular plasma proteins. The pore size distribution thereby indicates the likelihood of a pore at a specific pore size occurring among all the hollow fiber membrane's given pores. The maximum of the nominal pore size distribution thus predicates the specific pore size occurring most frequently among all the pores. Further demonstrated in the present case was that regulating the nominal pore size distribution during the production of a hollow fiber membrane such that the maximum of the nominal pore size distribution is in the range of 22 to 26 Å, preferentially from 23 to 26 Å, and the albumin sieving coefficient is in the range of less than 0.01, enables the production of a membrane of improved selectivity.

In a second aspect, the invention relates to a hollow fiber membrane filter. The hollow fiber membrane filter consists of a cylindrical housing containing a plurality of hollow fiber membranes. In particular, the hollow fiber membranes can be formulated in accordance with an implementation pursuant the first aspect of the invention. The hollow fiber membranes are sealed at the ends in the hollow fiber membrane filter with a casting compound such that a first chamber encompasses the interior space of the hollow fiber membrane and a second chamber encompasses the space between the hollow fiber membranes. The hollow fiber membrane filter further comprises a first fluid port for the supply of fluids, particularly liquids or gases, into the interior of the hollow fiber membranes and a second fluid port for draining liquids or gases from the interior of the hollow fiber membranes. The hollow fiber membrane filter is characterized by the hollow fiber membranes having an evenly distributed permeation property, in particular a uniform ultrafiltration coefficient, in different regions, in particular in a cross section of the hollow fiber membrane filter. The uniformity to the permeation property of the hollow fiber membranes in the different regions of the hollow fiber membrane filter is measured by the hollow fiber membranes, having ultrafiltration coefficients in different regions, differing from one another by no more than 20%.

The uniform ultrafiltration coefficient of the hollow fiber membranes in the hollow fiber membrane filter is attributed to a method step being employed in the production process which utilizes a transmembrane passage of a fluid, in particular water vapor or water. As defined by the present invention, water vapor refers to the designation of water in the gaseous aggregate state. Within the meaning of the present application, water vapor also refers to a form of gaseous water, that which is accompanied by so-called visible steam vapor; i.e. mist-like water droplets distributed throughout the air. Thus, also encompassed by the term water vapor as it is used in the present application are other sub-designations of water vapor such as, for example, superheated steam, wet steam, saturated steam, overheated steam and supercritical steam.

The transmembrane passage of the fluid can ensue from the first chamber, which comprises the interior of the hollow fiber membranes, into the second chamber, which comprises the space between the hollow fiber membranes, through the membrane wall. In an alternative implementation, the transmembrane passage can ensue through the membrane wall from the second chamber, which comprises the space between the hollow fiber membranes, into the first chamber, which comprises the interior of the hollow fiber membranes. It is assumed that the transmembrane passage can effect a flushing of the PVP pores so that any constricting or blocking of the hollow fiber membrane pores by deposited PVP which might occur in the production process can be eliminated. It is further assumed that an aggregating of the hollow fiber membranes is also eliminated by the transmembrane water and/or water vapor passage. With the transmembrane passage of the fluid, particularly the water vapor or water, from the interior of the hollow fiber membranes to the exterior of the hollow fiber membranes, the flowing fluid dissolves such aggregations from the inside of the fiber. An overall disaggregation of the hollow fiber membranes is thus observed within the hollow fiber membrane bundle. Fluid flowing into the hollow fiber membrane from the outside and passing through the membrane wall into the interior of the membrane likewise induces a disaggregating of hollow fiber membranes adhering together. It was further observed that the ultrafiltration coefficient, based on the hollow fiber membrane filter as a whole, rises.

A hollow fiber membrane filter in the sense of the second aspect of the invention can comprise 50 to 20,000 hollow fiber membranes, these being disposed at a packing density of 50 to 70% in the housing of the hollow fiber membrane filter. Packing density hereby refers to the space filled by hollow fiber membranes in a hollow fiber membrane bundle placed into the housing. The packing density of hollow fiber membranes is the sum of the cross-sectional areas of the individual hollow fiber membranes divided by the total cross-section area defining all the hollow fiber membrane cross-sectional areas in an arrangement. This is usually the cross section of the housing. With hollow fiber membranes and housing geometries of circular cross section, the packing density is calculated according to the following formula:

$$\delta_{(Packing\ density)} = \eta \cdot \frac{d^2_{(fiber)}}{d^2_{(Housing)}}$$

$d_{(Fiber)}$ is the mean outer diameter of the unloaded hollow fiber membrane $d_{(Filter)}$ is the inner diameter of the housing n: the number of hollow fiber membranes in the housing.

The term of unloaded hollow fiber membrane refers to an individual unencumbered hollow fiber membrane. The hollow fiber membrane can be deformed in the housing under the effect of compression; i.e. take on a deformed cross section under load. However, the diameter of the unloaded hollow fiber membrane is always used to calculate the packing density.

The disaggregating of the hollow fiber membrane filter by the transmembrane passage of the fluid during the manufacture of the hollow fiber membrane filter is thereby more effective in tightly packed cases; i.e. where hollow fiber membrane filters have a high packing density, than is the case with hollow fiber membrane filters having a low packing density. In particular, hollow fiber membrane disaggregation in hollow fiber membrane filters having a hollow fiber membrane packing density of 50 to 70%, preferentially 55 to 65%, further preferentially 55 to 65%, is regarded as particularly effective.

In particular, the transmembrane passing of the fluid, particularly water vapor or water, can be realized within the context of a heat sterilization procedure or can even be a part of a heat sterilization step. In the latter case, it is provided to use water vapor at a temperature of 121 to 140° C. so that germicidal sterilization will also occur with the transmembrane passage of the water vapor.

In a third aspect, the invention relates to a method for manufacturing hollow fiber membrane bundles for use in a hollow fiber membrane filter comprising a plurality of hollow fiber membranes. In particular, the hollow fiber membrane filter can be a hollow fiber membrane filter in accordance with an implementation of the second aspect of the invention; further particularly, the hollow fiber membranes can be formulated in accordance with an implementation of the first aspect of the invention. The production process comprises a spinning method for polysulfone and polyvinylpyrrolidone-based hollow fiber membranes; the spinning method is in particular a dry-wet spinning method. The production process comprises the method steps of:

Providing a spinning solution comprising a polysulfone-based material, in particular polysulfone, a vinylpyrrolidone-based polymer, in particular polyvinylpyrrolidone, an aprotic solvent, in particular dimethylacetamide, Providing a coagulant liquid comprising water and an aprotic solvent, in particular dimethylacetamide, Co-extruding the spinning solution and the coagulant liquid through a concentric annular spinneret into a hollow strand, whereby the cavity of the strand is filled with coagulant liquid, Conducting the strand through a precipitation gap, Introducing the strand into a precipitating bath comprised substantially of water so as to obtain a hollow fiber membrane, Conducting the hollow fiber membranes through at least one rinsing bath and drying the hollow fiber membrane obtained, Arranging the resulting hollow fiber membranes into a hollow fiber membrane bundle, Treating the hollow fiber membrane bundle with water vapor.

The method is further characterized by the water vapor treatment comprising at least one step in which water vapor is conducted into the interior of the fibers and permeates through the membrane wall to the exterior of the fibers under the application of pressure.

After the hollow fiber membranes have been arranged into a hollow fiber membrane bundle and prior to treating the hollow fiber membrane bundle with water vapor, the hollow fiber membrane bundle can be placed into a housing of a hollow fiber membrane filter and cast with a curable resin at the ends of the hollow fiber membrane bundle in accordance with known prior art methods.

The hollow fiber membrane bundle cast into the housing can be further processed into a hollow fiber membrane filter such that two fluid flow chambers are formed, whereby a first chamber encompasses the interior of the hollow fiber membranes and a second chamber encompasses the space between the fibers, and wherein the hollow fiber membrane filter has at least one port for fluids into the first chamber of the hollow fiber membrane filter and at least one port for fluids into the second chamber of the hollow fiber membrane filter. The steam treatment step of the hollow fiber membrane bundle can then be realized in the interior of the hollow fiber membrane filter by introducing water vapor into the first chamber of the hollow fiber membrane filter encompassing the interior of the hollow fiber membranes through the first fluid port and passing it through the membrane wall into the second chamber of the hollow fiber membrane filter encompassing the space between the hollow fiber membranes under the application of pressure, and guiding it out of the second chamber via the second port on the hollow fiber membrane filter.

The water vapor treatment step can be realized in the course of a rinsing process or in the course of heat sterilization; in particular, the water vapor treatment step itself constitutes a rinsing step when the hollow fiber membranes are incorporated into a hollow fiber membrane filter as a hollow fiber membrane bundle.

Manufacturing a hollow fiber membrane filter according to the above-cited method enables a hollow fiber membrane filter to be produced in which its hollow fiber membrane pores are free of PVP blockages or constrictions and in which the individual hollow fiber membranes do not cluster together. This has the consequence of increasing the clearance of the hollow fiber membranes in a hollow fiber membrane filter produced in accordance with the inventive method since a larger membrane surface is effectively provided for the transmembrane exchange of material by the individual fibers and the pores being cleared of deposited PVP.

The manufacturing method further ensures excellent hollow fiber membrane biocompatibility when the water vapor treatment step is performed in the course of heat sterilization. In this case, the destroyed cell fragments and endotoxins ensuing under the sterilization conditions are flushed from the membrane surface. It is thus provided in a preferential embodiment for the hollow fiber membrane bundle to be further processed into a filter prior to the water vapor treatment step and the water vapor treatment be performed on the hollow fiber membrane filter during the course of a sterilization step.

In a further implementation of the third aspect of the invention, a spinning solution is used for the spinning process on the hollow fiber membranes which comprises a ratio of 14 to 18% of a polysulfone-based polymer, preferably polysulfone, and a 3 to 6% ratio of a vinylpyrrolidone-based polymer, preferably polyvinylpyrrolidone. A polar aprotic solvent, preferentially dimethylacetamide (DMAC) constitutes a further percentage of the spinning solution.

In a further implementation of the third aspect of the invention, the inventive method for producing a hollow fiber membrane bundle is characterized by the coagulant liquid comprising 25% to 40% of a polar aprotic solvent, in particular dimethylacetamide, particularly 25% to 40% DMAC and 60 to 75% water.

In a further implementation of the third aspect of the invention, the inventive method for producing a hollow fiber membrane bundle is characterized by the precipitating bath being temperature-controlled to 75° C. to 85° C. in the spinning process. This precipitating bath temperature contributes to a high ultrafiltration coefficient and a high sieving coefficient for molecules in the mid-molecular weight range.

In a further implementation according to the third aspect of the invention, the inventive method for producing a hollow fiber membrane bundle is characterized by the hollow fiber membranes being washed at a temperature of from 75° C. to 90° C. In the washing process, wash liquid, preferentially water, is channeled into the hollow fiber membrane filter and the filter in the first chamber and in the second chamber is rinsed with water. This process flushes residual particles and elutable elements of the hollow fiber membrane and the filter housing out of the hollow fiber membrane filter.

In a further embodiment according to the third aspect of the invention, the inventive method for producing a hollow fiber membrane bundle is characterized by the hollow fiber membranes being dried at a temperature of 100° C. to 150° C.

In a further embodiment according to the third aspect of the invention, the inventive method is characterized by the water vapor treatment of the hollow fiber membrane bundle being performed at a temperature of more than 60° C. to 140° C.

In a fourth aspect, the invention relates to a sterilization procedure for sterilizing a hollow fiber membrane filter. According thereto, a hollow fiber membrane filter is sterilized which comprises a plurality of hollow fiber membranes sealed at the ends in the housing of the hollow fiber membrane filter such that a first chamber is formed which encompasses the interior of the hollow fiber membranes and a second chamber is formed which encompasses a space between the hollow fiber membranes. The hollow fiber membrane filter further comprises at least two fluid ports connected to the first chamber and at least two fluid ports connected to the second chamber, whereby the fluid ports are disposed so as to be connected to a sterilizing device, and wherein the method comprises at least the steps of:

Rinsing the hollow fiber membrane filter with a fluid, particularly water, whereby the rinsing fluid is routed through the first and the second chamber of the hollow fiber membrane filter by the selection of the fluid ports, Sterilizing the hollow fiber membrane filter with a sterilizing fluid, particularly water or water vapor, whereby the sterilizing fluid is channeled through the first and the second chamber of the hollow fiber membrane filter by the selection of the fluid ports, Supplying a fluid, particularly water or water vapor, into the first or second chamber of the hollow fiber membrane filter by the selection of the fluid ports, and Transmembrane passing of the fluid, particularly water or water vapor, across the membrane wall into the respective second or first chamber of the hollow fiber membrane filter.

One embodiment of the inventive method according to the fourth aspect of the invention provides for a rinsing step to be performed on the hollow fiber membranes incorporated into the hollow fiber membrane filter employing sterile water or water vapor, respectively sterilizing water or water vapor. Sterilizing in this case means that the rinsing steps are performed under thermal and pressure conditions. Sterilizing conditions in the context of heat sterilization of hollow fiber membrane filters are present at temperatures of more than 105° C. to 150° C., preferentially 121° C. and 140° C., and an absolute pressure of 1.1 bar to 10 bar, preferably 2 bar to 4 bar.

In a further embodiment of the fourth aspect of the invention, the inventive method comprises a step in which a fluid, particularly water or water vapor, is introduced into the first chamber of a filter module, transported across the membrane wall into the second chamber by an induced pressure difference, and drained off from there. Alternatively, the fluid, particularly water or water vapor, can also be channeled into the second chamber of the hollow fiber membrane filter by a selection of the fluid port and routed across the membrane wall from the second chamber into the first chamber of the hollow fiber membrane filter by an induced pressure difference. The fluid ports of the hollow fiber membrane filter are thereby connected to a sterilizing apparatus able to convey sterilizing fluids, in particular heated water and/or water vapor, to the hollow fiber membrane filter. Preferably, the fluid, in particular water or water vapor, is conveyed into the first chamber through a first fluid port and a further fluid port to the first chamber of the hollow fiber membrane filter, if applicable, is blocked. Fluid, in particular water or water vapor, can however also be conveyed into the hollow fiber membrane filter through both fluid ports simultaneously. In both cases, a buildup of pressure from conveying the fluid, in particular water or water vapor, causes the fluid, in particular water or water vapor, to pass through the membrane wall and enter the second chamber. In the second chamber, the fluid, in particular water or water vapor, which has passed through can be drained via a further fluid port.

In a further embodiment of the fourth aspect of the invention, it is recognized that the transmembrane passage of the fluid, in particular water or water vapor, preferentially occurs prior to a sterilization process.

In a further embodiment of the fourth aspect of the invention, the sterilization of the hollow fiber membrane filter ensues by way of feeding in a sterilizing liquid through two fluid ports which are provided for supplying fluids into the first chamber and the second chamber of the hollow fiber membrane filter. The fluids are drained out of the first chamber and the second chamber of the hollow fiber membrane filter via two respective further fluid ports for draining fluids such that the sterilizing liquid flushes out the two chambers and the filter. Preferably sterile water which is temperature-controlled to a temperature of 105° C. to 140° C. serves as the sterilizing liquid.

A further embodiment of the fourth aspect of the invention can provide for a rinsing operation with a fluid, in particular sterile water. Alternatively, aqueous mixtures can be employed as the rinsing liquid. Preferentially, the rinsing occurs at increased temperature. The rinsing liquid can thereby preferentially be at temperatures from 50° C. to 120° C. The rinsing operation is in particular able to better remove particles and further elutable substances at increased temperature. Should the membrane material also comprise hydrophilic elements, an excessively high temperature in the rinsing operation is undesirable as too much adhering of the membrane material can be initiated. A preferential rinsing temperature is 60 to 98° C., the temperature of 70 to 98° C. is particularly preferential.

Sterilization with water vapor ensues at temperatures of 124° C.±5° C. A technical system cannot always precisely maintain a preselected temperature. It has therefore proven technically expedient to select temperatures between 105° C. and 140° C. Pressures of up to 4 bar are thereby set. At a sterilization temperature of 124° C., the required sterility can be achieved within 12 minutes. Alternatively, sterilization can also occur at lower temperatures for longer sterilizing periods, e.g. at 121° C. for 15 minutes.

The transmembrane passage of a fluid, e.g. water or water vapor, preferably occurs at increased temperatures. Water vapor in sterile form is thereby preferentially used. In particular, transmembrane water vapor passage at temperatures of 50° C. to 98° C. can also flush particles and elutable substances from the membrane wall and the inner pore surfaces not directly on the membrane surface.

Proven advantageous for the sterilization and rinsing process as a whole is for a flushing step with compressed air or an alternative compressed gas to occur in between the first rinsing step with a rinsing fluid, in particular water or water vapor. In the process, sterile compressed air is used to exhaust both chambers of the filter module without creating a pressure gradient over the membrane material between the first and second chamber. Liquid from the preceding rinsing process thereby remains in the pores. This intermediate step facilitates the following transmembrane flushing procedure. This further embodiment of the fourth aspect of the inventive is thus characterized by the effecting of a further flushing operation with compressed gas, in particular sterile compressed air.

DESCRIPTION OF THE INVENTION BASED ON MEASUREMENT METHODS, FIGURES AND EXAMPLES

Measurement Method 1: Determining Porosity

A hollow fiber membrane bundle having previously been dried for 2 hours at 105° C. in a drying cabinet and consisting of identical hollow fiber membranes is weighed. The mean length of the fibers, the average inner diameter and average outer diameter and the number of fibers is determined. The mean dimensions are determined for at least 10 different fibers of the hollow fiber membrane bundle. The determining of the dimensions occurs at a constant temperature of 20° C. A volume osmosed through the membrane walls of the hollow fiber membranes of the hollow fiber membrane bundle is calculated from the dimensions by assuming that the geometry of the hollow fiber membranes corresponds to a hollow cylinder. From the volume as ascertained and the measured weight, the average density of the membrane structure within the hollow fiber membranes can be calculated. The porosity expressed as a percentage results from the ratio between determined and theoretical hollow fiber membrane density at full polysulfone material compactness pursuant to the following formula:

$$\text{Porosity} = \frac{\text{measured fiber density}}{\text{compact polysulfone density}} \cdot 100$$

Measurement Method 2: Determining Zeta Potential

Figure 2:
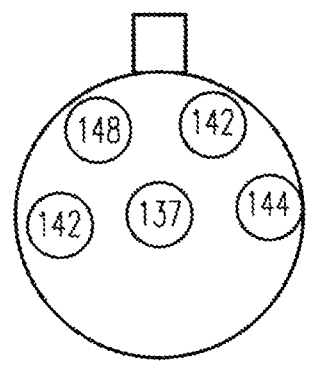
FIG. 2 shows a schematic depiction of the cross-sectional areas of a hollow fiber membrane filter.

To determine the zeta potential of the hollow fiber membranes under assessment, a hollow fiber membrane filter (dialyzer) having 10,752 hollow fiber membranes of an inner diameter of 185 µm and a wall thickness of 35 µm is used. The length of the hollow fiber membranes relevant to measuring the zeta potential is 279 mm. The hollow fiber membranes are sealed at the ends in the hollow fiber membrane filter so as to create a first chamber encompassing the interior of the hollow fiber membranes and to create a second chamber encompassing the space between the hollow fiber membranes. Polyurethane from the Elastogran company (polyol C6947 and isocyanate 136-20) is used as the casting material. The casting height at each bundle end amounts to 22 mm. An apparatus in accordance with FIG. 1 is used for the measurement. The hollow fiber membrane filter (1) comprises fluid ports (2, 2a, 3, 3a) to the respective first and second chamber of the hollow fiber membrane filter (1). The fluid ports to the first chamber of the hollow fiber membrane filter (1) are each provided with an Ag/AgCl electrode (4, 4a) and a port for the pressure gauge (5, 5a). The fluid ports (3, 3a) to the second chamber of the hollow fiber membrane filter (1) are tightly sealed so that the second chamber of the hollow fiber membrane filter is unfilled. The potential difference $\Delta E_z$ (mV) is thus registered between the two electrodes by a voltmeter (6), the decrease in pressure $\Delta P$ (N/m²) between the accessways for the pressure gauge (5, 5a) registered by a manometer (7). The test liquid consists of a 1 molar KCl solution in water at a pH value of 7.4 and is provided in a reservoir (8) positioned approximately 1000 mm above the filter. The pH value is set pursuant to the following rule: 50 mg $K_2CO_3$ is added to 100 liters of the KCl solution. The mixture is stirred in an open container until reaching a pH value of 7.4. The container is then tightly sealed. The measurement is performed at a temperature of 23° C.+/−2° C.

To measure the zeta potential, the test liquid is poured through a first fluid port (2) into the first chamber of the hollow fiber membrane filter which encompasses the interior space of the hollow fiber membranes and is routed out of the dialyzer again through a second fluid port (2a) on the hollow fiber membrane filter connected to the interior space of the hollow fiber membranes. The hollow fiber membrane filter is initially flushed with the test liquid in this configuration for 10 min. until a stable value is reached, and if need be for an additional 5 min. The pressure difference and the potential difference are at the same time read from the manometer and multimeter respectively and the zeta potential calculated therefrom. To increase the measurement accuracy, it is provided to switch the two 4-way valves subsequent the measured value acquisition so as to yield a reverse flow of the test liquid through the interior space of the hollow fiber membranes. The measured value for the zeta potential is then formed from the mean measurement value in both flow directions.

The zeta potential calculation is derived from the following equation:

$$\zeta = \frac{\eta * \Lambda o * dEz}{\varepsilon o * \varepsilon r * d\Delta P}$$

where $\zeta$=zeta potential (mV)
$\eta$=solution viscosity (0.001 Ns/m²)
$\Lambda_o$=solution conductivity (A/(V*m))
$\varepsilon_o$=vacuum permittivity (8.85*10⁻¹² A*s/(V*m))
$\varepsilon_r$=relative solution permittivity (80)
$E_z$=flow potential (mV)
$\Delta_P$=pressure difference (N/m²)

Measurement Method 3: Determining the Dextran Sieving Coefficient

A hollow fiber membrane's dextran sieving coefficient is measured according to DIN EN ISO 8637:2014 on a fully constructed hollow fiber membrane filter. According thereto, a filter having 10,752 hollow fiber membranes of an inner diameter of 185 µm and a wall thickness of 35 µm is used. The active length of the hollow fiber membrane amounts to 235 mm. An active length of a hollow fiber membrane is to be understood as the length of the hollow fiber membrane without casting compound able to be used for determining the permeation properties such as sieving coefficient, clearance and ultrafiltration coefficient. The inner diameter of the hollow fiber membrane filter is 34 mm at the center. The hollow fiber membrane filter otherwise exhibits the same structure as described in "measurement method 2." In departure from the standard, an aqueous dextran solution having a broad molecular weight distribution of the dissolved dextran between 1000 and 10,0000 Da or a mixture of several dextrans within this molecular weight range is used as the test liquid so as to yield the indicated molecular weight distribution. The dextran solution is passed through the fluid ports, through the first chamber of the hollow fiber membrane filter encompassing the interior of the hollow fiber membranes at a flow of 446.6 ml/min. A pure water flow of 89.9 ml/min via the fluid ports is set in the second chamber of the hollow fiber membrane filter. After 12 minutes, the dextran concentration is determined depending on the respective molecular weight at the first and second fluid port of the first chamber of the hollow fiber membrane filter over the entire molecular weight range by means of gel permeation chromatography and a sieving coefficient curve over the entire molecular weight range determined therefrom The sieving coefficient of a dextran molecule at a specific molecular weight can then be determined from the sieving coefficient curve.

Measurement Method 4: Determining the Albumin Sieving Coefficient

The albumin sieving coefficient of a hollow fiber membrane is undertaken on a filter as in measurement method 3. In the measurement, a human plasma is used pursuant the DIN EN ISO 8637:2014 standard to determine the sieving coefficient. Thus determined is the "plasma sieving coefficient" of the albumin. The Cobas Integra 400 plus analyzer from the Roche Diagnostics GmbH company, Mannheim, is used as the analytical device. The measurement is conducted by means of the ALBT2 test in the urine application. A plasma flow of 446.6 ml/min. and a dialysate flow (deionized water) of 89.9 ml/min. is established.

Measurement Method 5: Determining the Sodium, Phosphate and Vitamin B12 Clearance The clearance of a hollow fiber membrane is determined on the basis of a hollow fiber membrane filter structured as per measurement method 2 according to DIN EN ISO 8637:2014. Pursuant to 5.6.1.2 of the standard, aqueous sodium solutions at a concentration of 5 g/l NaCl and 0.05 g/l Vit B12 Vitamin B12 are used as test solutions for the blood area (blood area corresponds to the first chamber of the hollow fiber membrane filter encompassing the interior of the hollow fiber membranes); distilled water is hereby used for the dialysis fluid area (dialysis fluid area corresponds to the second chamber of the hollow fiber membrane filter encompassing the fiber interspace). Phosphate is used at a concentration of 3 mmol/l in the dialysis fluid, the measurement is likewise carried out against dialysis fluid on the dialysate side. For phosphate, the following dialysis fluid is prepared: 34.63 l water, 102.9 g $NaHCO_3$, 210.68 g NaCl, 2.61 g KCl, 5.15 g $CaCl_2*2 H_2O$, 3.56 g $MgCl_2*6H_2O$, 6.31 g $CH_3COOH$, 38.5 g glucose monohydrate. Phosphate is determined photometrically following reaction with ammonium molybdate in sulphuric solution, whereby the Cobas integra 400 plus device from the Roche Diagnostics GmbH company, Mannheim, Germany, and the (Roche) PHOS2 test is used. The sodium concentration is determined by measuring conductivity. The vitamin B12 concentration is determined photometrically. The clearance tests make use of an identically structured hollow fiber membrane filter as is also used in the measurement pursuant measurement method 2. A flow of 300 ml/min is set in the first chamber of the hollow fiber membrane filter encompassing the interior of the hollow fiber membranes for the hollow fiber membrane filter produced within the scope of the present application, a flow of 500 ml/min is set in the second chamber of the hollow fiber membrane filter.

Measurement Method 6: Determining the Local Ultrafiltration Coefficient

A hollow fiber membrane filter with 10,752 hollow fiber membranes of an inner diameter of 185 µm and a wall thickness of 35 µm as described in "measurement method 3" is used in determining the local ultrafiltration coefficient. The active length of the hollow fiber membrane amounts to 235 mm. The active length of the hollow fiber membrane is to be understood as the length of the hollow fiber membrane without casting compound able to be used for determining the permeation properties such as sieving coefficient, clearance and ultrafiltration coefficient. The inner diameter of the hollow fiber membrane filter is 34 mm at the center. The inlet cap of the blood side of the filter is removed from the hollow fiber membrane module and replaced by an inlet containing an apparatus which directs the flow of the test liquid to only one circular portion of the hollow fiber bundle having a diameter of 1 cm. In departure from the DIN ISO 8637:2014 standard, water is thereby used as the test liquid, hence determined is the "aqueous ultrafiltration coefficient" as known to one skilled in the art. This apparatus is designed such that the end of the apparatus penetrates approximately 3 mm into the upper end of the hollow fiber membrane bundle and thus results in sealing the apparatus with respect to the hollow fiber membrane bundle. Doing so thus ensures that only a local circular surface area of 1 cm in diameter is measured. To measure further areas, either a modified apparatus is used or the apparatus is repositioned at the desired location. A schematic depiction of the cross-sectional areas of a hollow fiber membrane filter can be seen in FIG. 2. When setting the flows of the test liquid, care is taken to set the same transmembrane pressures (TMP) as in the measurement of the aqueous ultrafiltration coefficient based on DIN ISO 8637:2014. The highest set TMP is 600 mm Hg.

Measurement Method 7: Determining the Hollow Fiber Membrane PVP Content

The PVP content of the hollow fiber membrane is determined by means of IR spectroscopy. In the process, the sample is first dried for 2 hours in a drying cabinet at 105° C. 1 g of the fiber is then dissolved in dichloromethane. Calibration standards using dried PVP, which is likewise dissolved in dichloromethane, are additionally established. A concentration range of approximately 1% to 10% PVP in the hollow fiber is thereby covered. The solutions are each put into a fluid cuvette to a layer thickness of 0.2 mm. The absorption band of the carbonyl function is used for the assessment.

Measurement Method 8: Depicting the Nominal Pore Size Distribution and the Nominal Average Pore Size A measure of the pore size distribution of an inventive membrane can be derived starting from the sieving coefficient curve as depicted in FIG. 7. To this end, the sieving coefficient curve, as described in measurement method 3, is obtained for a dextran sample or a mixture of multiple dextran samples broadly distributed in molecular weight. For each molecular weight, the sieving coefficient curve provides a passage probability for the respective dextran molecule passing through the membrane wall. Given a specific temperature and specific solvent, molecular weight correlates to a specific molecule size which can be defined by the Stokes radius. The relationship between Stokes radius and molecular weight yields the J. Bandrup, E. H. Immergut equation ("Polymer Handbook" (1989) VII pp. 112-113, John Wiley):

$$\text{Stokes Radius}[\text{Å}] = 0.4456 \cdot M^{0.43821}$$

wherein M stands for the molecular weight of the dextran. The molecular weight is converted into the Stokes radius for each data point of the sieving coefficient curve pursuant FIG. 7, by means of, for example, computer software, e.g. the "Excel" program. A corresponding depiction similar to the sieving coefficient curve depicts a passage probability at which the dextran molecule at a specific Stokes radius; i.e. a specific molecular size, is able to pass the membrane wall. At the same time, this depiction provides information about the structure of the pore size distribution by thereby indicating how high a probability there is of having a membrane pore of specific size so as to allow passage of a dextran molecule of predetermined molecular size; i.e. Stokes radius.

Further, conversion with the Excel software program is used to establish the first derivative at each point of the curve. The resultant curve progression thereby indicates a distribution curve which depicts a measure of nominal pore size distribution for the membrane being assessed. A corresponding curve progression is shown in FIG. 8 for a membrane according to the invention and for a comparative membrane. The maximum of the distribution curve depicts a nominal average pore size of the membranes.

Example 1: Method for Purifying a Hollow Fiber Membrane Filter

Figure 3:
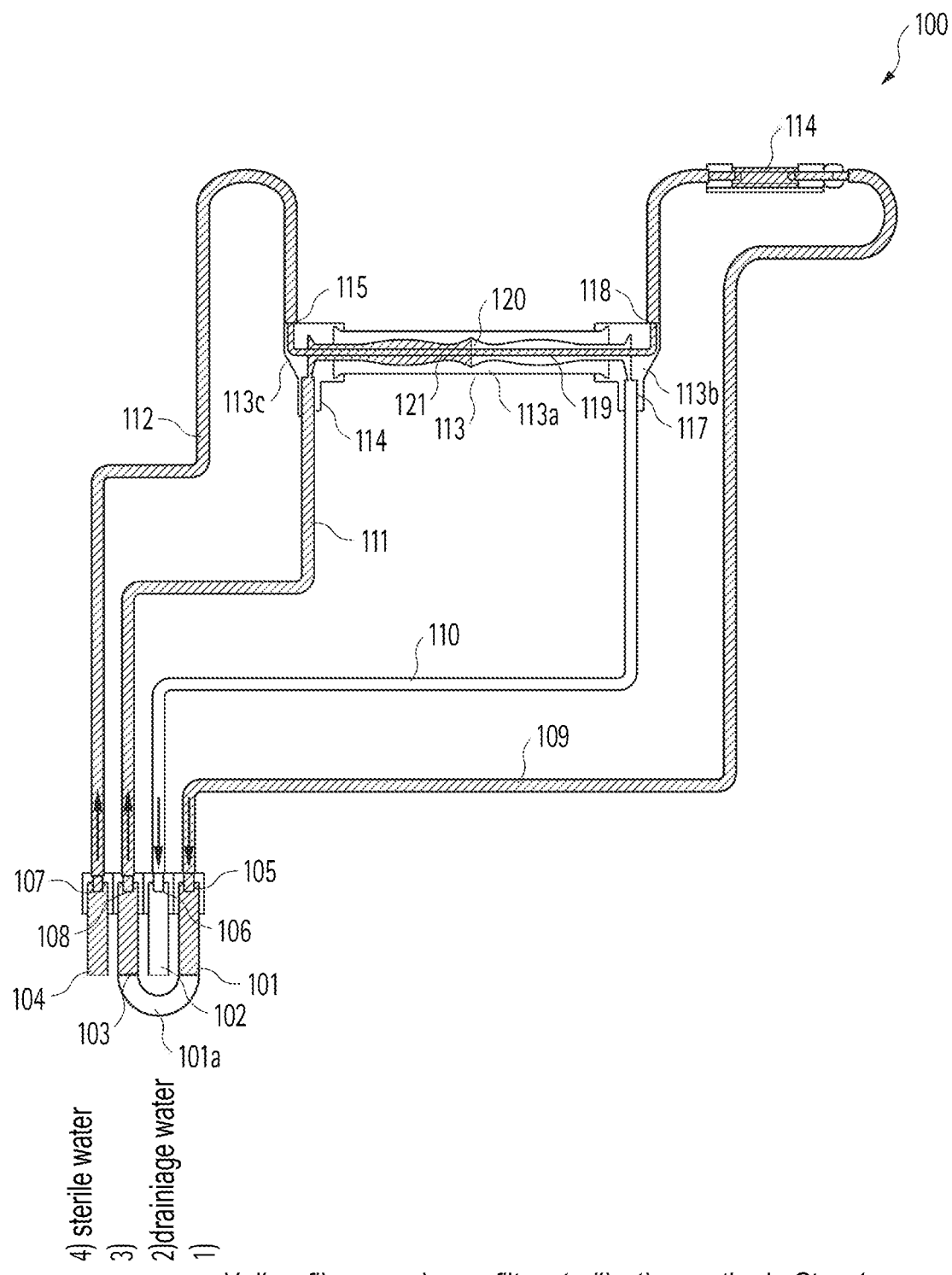
FIG. 3 is a diagram that schematically depicts a first step of a purification procedure for a hollow fiber membrane.

FIG. 3 schematically depicts a first step of a purification procedure for a hollow fiber membrane comprising rinsing and sterilization steps as is used in the production of hollow fiber membranes according to the invention, respectively hollow fiber membrane filters according to the first, second and third aspect of the invention. FIG. 3 shows a fluid port 118 to a first chamber 119 of a hollow fiber membrane filter 113 encompassing the interior of the hollow fiber membranes, which is fluidly connected to a connection 101 by means of a line 109 having a valve 105. A further fluid port 117 is fluidly connected to connection 102 via line 110, valve 106, and forms an inlet to a second chamber 120 of the hollow fiber membrane filter 113 encompassing a space between the hollow fiber membranes. A further fluid port 114 is in fluidic connection via line 111 with valve 107 and connection 103 and forms an inlet to a second chamber 120 of the hollow fiber membrane filter. Fluid port 115 is in fluidic connection via line 112 with valve 108 and connection 104. Connection 101 and 103 are further in fluidic connection via connector 101*a*.

In one example implementation of a rinsing procedure, a rinsing liquid is conveyed to the hollow fiber membrane filter 113 through line 112 via connection 104 in the first step as depicted. Preferably, the rinsing liquid is temperature-controlled sterile water, whereby temperatures of 50 to 98° C. are maintained. Valve 108 is thereby switched to flow-through. The rinsing liquid flows into the first chamber 119 of the hollow fiber membrane filter via the second fluid port 115 and exits said first chamber via the first fluid port 118. The arrangement enables rinsing the interior of all the hollow fiber membranes of a hollow fiber membrane bundle.

The rinsing liquid further passes through a bubble detector 114, which assumes no function in this rinsing operation, and line 109, and is directed through connection 101 and connector 101*a* to line 111. The rinsing liquid enters into the second chamber 120 of the filter module 113 via fluid port 114 and flushes the second chamber formed in the space between the hollow fiber membranes. A return flow of the flushing liquid occurs via fluid port 117 and line 110 which is then either discarded or treated so as to again be available for a further rinsing operation.

Figure 4:
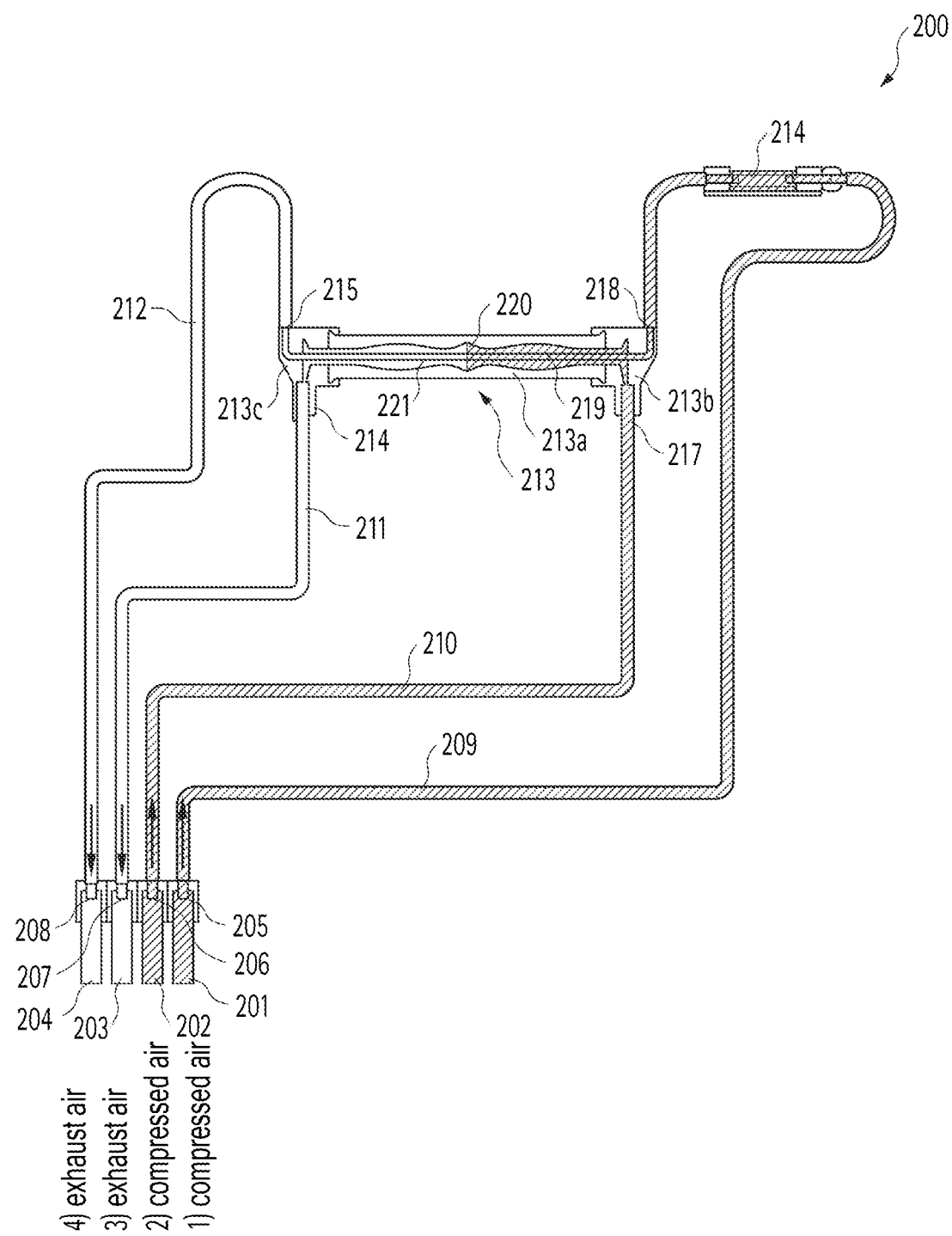
FIG. 4 is a diagram that schematically depicts a second step in a rinsing and sterilization procedure as is used in the production of hollow fiber membranes according to the invention.

FIG. 4 schematically depicts a second step in a rinsing and sterilization procedure as is used in the production of hollow fiber membranes according to the invention, respectively inventive hollow fiber membrane filters according to the first, second and third aspect of the invention. FIG. 4 is hereby used to illustrate compressed air flushing. A compressed air source feeding sterile air supplies connections 201, 202. The compressed air is conveyed through lines 209 and 201 via the open valves 205 and 206 and to the hollow fiber membrane module 213 by not shown pumping means. The first chamber 219 and the second chamber 220 are initially still filled with water from the preceding rinsing step of the rinsing operation pursuant to FIG. 3. Valves 207 and 208 are open and prepared for a discharge of rinsing liquid. The compressed air is conveyed through the filter module at a pressure of 1.5 to 2 bar. Via the respective fluid ports 218, 217, the compressed air thereby further transports residual water out of the first and second chamber of the hollow fiber membrane filter through the respective fluid ports 215 and 214 to the return flow portion of the flow path circuit. Residual water and compressed air are drained off via lines 212, 211. The rinsing process runs for 2 to 5 minutes. Since equal pressure prevails in both chambers 219 and 220, there is no flushing across the membrane wall. In consequence, the pores of the membrane wall remain filled with water from the rinsing procedure.

Figure 5:
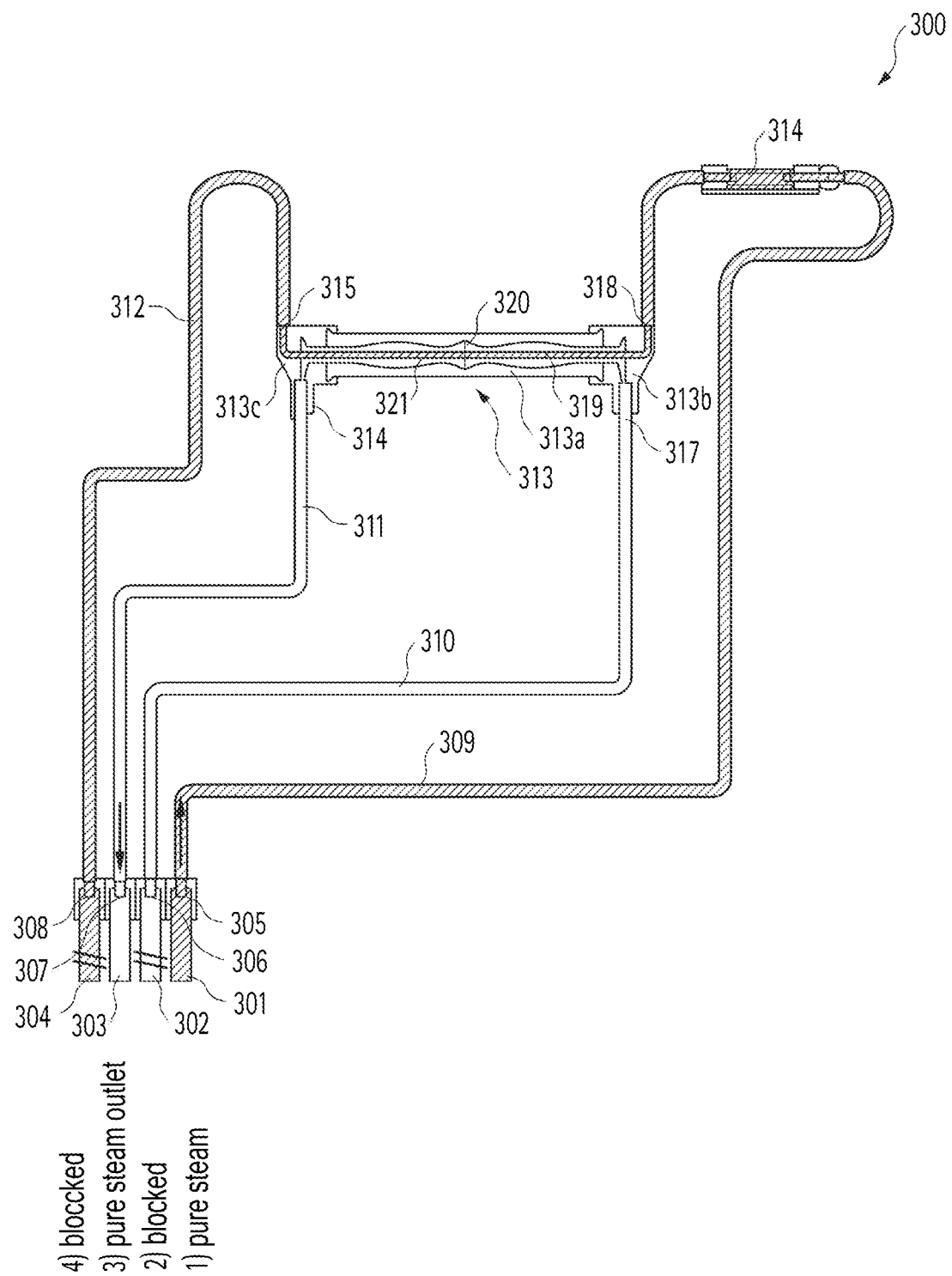
FIG. 5 is a diagram that schematically depicts a third step in a rinsing and sterilization procedure as is used in the production of hollow fiber membranes according to the invention.

FIG. 5 schematically depicts a third step in a rinsing and sterilization procedure as is used in the production of hollow fiber membranes according to the invention, respectively inventive hollow fiber membrane filters according to the first, second and third aspect of the invention. FIG. 5 depicts the connections 302 and 304 which block the drainage of rinsing fluids by valves 306 and 308 being in a closed valve position. Water vapor is conveyed into the sterilization system via connection 301 and to the filter module 313 via line 309. The water vapor disperses in the first chamber 319 of the hollow fiber membrane filter; drainage via fluid port 315 is not possible since connection 304 is blocked. Water vapor dispersal in line 312 can only ensue by compressing the pressurized pure steam or by diffusion.

Since there is a higher pressure in the first chamber than in the second chamber, a transmembrane passage of pure steam occurs. Residual water remaining in the pores from the rinsing process according to the first step of the rinsing and sterilization operation pursuant to FIG. 3 is evacuated and transported in line 311 through the second chamber 320. Due to connection 302 being closed, line 310 does not thereby serve in conveying fluid. Adjacent hollow fiber membranes are largely separated from one another by the transmembrane flushing procedure. Water vapor is thereby conveyed into the filter module at a pressure of 1.3 to 2 bar. The thorough flushing of the pores additionally prevents adhesion of the hollow fibers. This rinsing process can be terminated after a few minutes. In particular, the rinsing procedure is performed for 2 to 5 minutes. Temperatures are kept at 50° C. to 98° C., particularly also to thermally condition the filter module for the following sterilization procedure.

Figure 6:
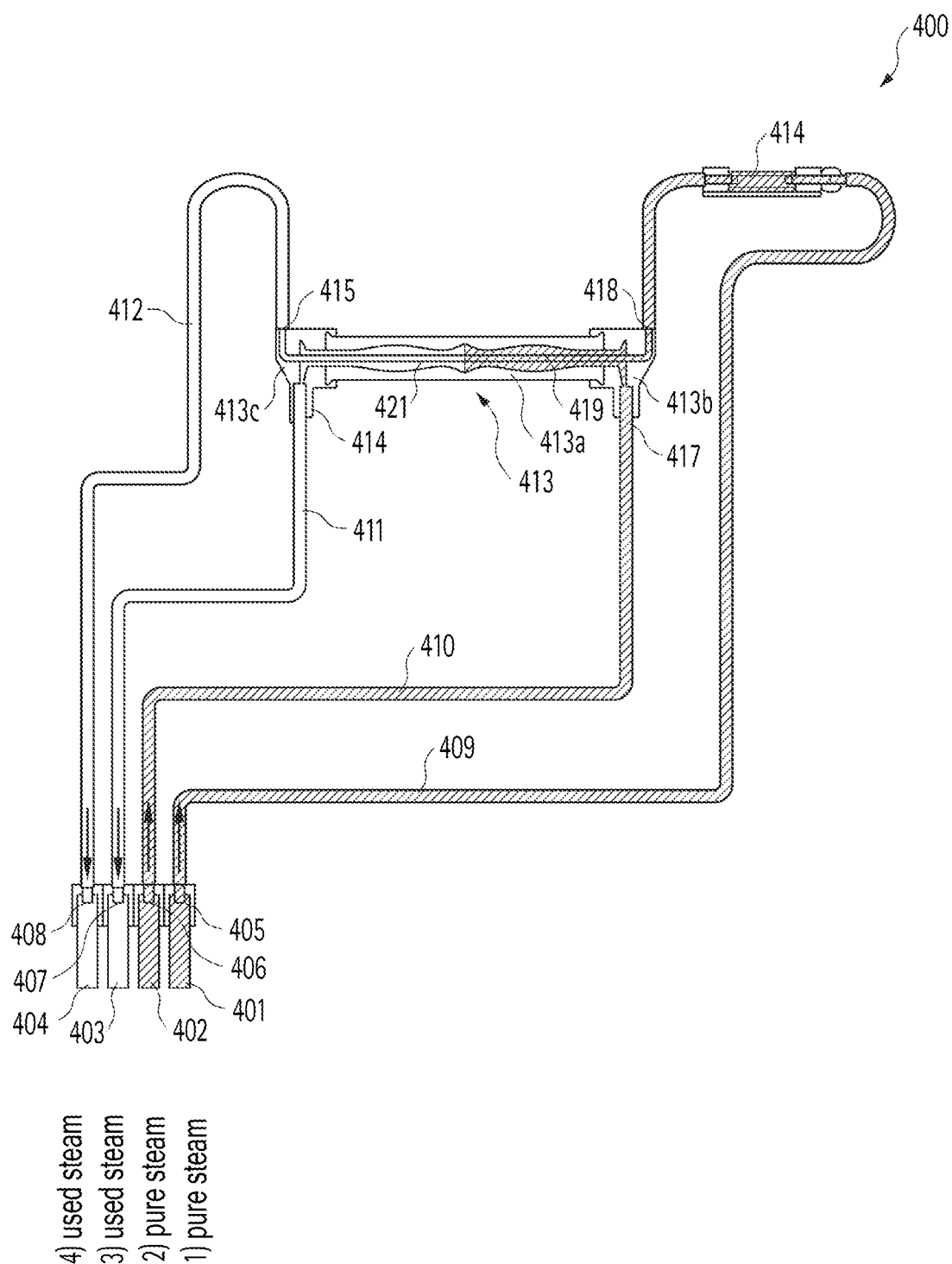
FIG. 6 is a diagram that schematically depicts a fourth step in a rinsing and sterilization procedure as is used in the production of hollow fiber membranes according to the invention.

FIG. 6 schematically depicts a fourth step in a rinsing and sterilization procedure as is used in the production of hollow fiber membranes according to the invention, respectively inventive hollow fiber membrane filters according to the first, second and third aspect of the invention. According to the fourth step, a sterilizing fluid such as, for example, water vapor at a temperature of 124° C. and a pressure of 2 bar is conveyed into the hollow fiber membrane filter. Flow-through is thereby possible through connections 401, 402, 403, 404 by way of the open valves 405 to 408. The pure steam is conveyed to the hollow fiber membrane filter via lines 409 and 410 and the first chamber 419 and the second chamber 420 of the filter module 413 flushed. The pure steam is returned via lines 412 and 411 and fluid ports 415 and 414 and is either discarded or treated for reuse. Depending on the sterilization temperature selected, the sterilization procedure can last 5 to 30 minutes. At the preferential temperature of 124° C., sterilization can be considered completed after 12 minutes. Further flushing steps can follow in order to bring the hollow fiber membrane filter into a purified and sterile form for use.

For the further quality testing, a "bubble point" test as known from the prior art follows. This test constitutes a pressure hold test in which one side of a membrane is subjected to gas at a higher pressure than the opposite side of the membrane with the fluid flow. The second chamber 120, 220, 320, 420 of the hollow fiber membrane filter shown in FIG. 3 to FIG. 6 is thereby flushed with sterile compressed air, whereby the first chamber remains filled with liquid from the rinsing process. The sterilization system applies a higher pressure in the second chamber than in the first chamber 119, 219, 319, 419. Since the pores are filled with water from the preceding rinsing step, the compressed gas from the first chamber does not breach the second chamber until the pressure applied overcomes the surface tension of the water in the pores. The volume of gas passing into the first chamber can be analyzed in the bubble detectors 114, 214, 314, 414 as shown and the results evaluated accordingly. By correlating the volume of gas bubbles detected to an applied pressure in the second chamber of the filter modules 120 to 420, conclusions can be drawn as to the quality of the membrane material and decisions made as to whether the filter module meets the specification standards.

It can subsequently be provided for the first chamber to likewise be flushed with sterile compressed air. In appropriate cases, a further flushing step with pure steam can ensure the removal of water remaining from preceding rinsing processes. Thereafter, a drying process can occur in which the filter module is flushed with sterile compressed air until a desired degree of dryness is reached.

Example 2: Example Embodiment of an Inventive Hollow Fiber Membrane

A spinning solution consisting of 16 parts by weight polysulfone (P3500 from the Solvay company), 4.4 parts by weight polyvinylpyrrolidone (K82-86 from the Ashland company) and 79.6 parts by weight DMAC is stirred, heated to 60° C. and degassed so as to process it into a homogeneous spin mass. The spin mass is extruded through an annular spinneret with a centrally controlled precipitant consisting of 35% DMAC and 65% water into a strand. The precipitant is channeled inside the hollow strand. The temperature of the annular spinneret is 70° C. The extruded strand is guided through a precipitation chamber, the atmosphere of which is at a relative humidity of 100%. The height of the precipitation gap is 200 mm; a precipitation gap dwell time of 0.4 sec. is set. The strand is introduced into the precipitating bath consisting of water which is temperature-controlled to 80° C. and precipitated into a hollow fiber membrane. The hollow fiber membrane is then routed through rinsing baths which are temperature-controlled to a temperature of 75° C. to 90° C. The hollow fiber membrane thereafter undergoes a drying process between 100° C. and 150° C. The hollow fiber membrane obtained is then taken up on a coiler and formed into a tow. Hollow fiber membrane bundles are produced from the coiled tow. The porosity of the hollow fiber membrane is thereafter determined.

The hollow fiber membrane bundle is further processed into hollow fiber membrane filters using known techniques as indicated in measurement method 3. The hollow fiber membrane filter obtained is connected in the next step to a sterilizing apparatus pursuant to example 1 and the hollow fiber membrane filter sterilized according to the method described in example 1. The sieving coefficient for a dextran at a molecular weight of 10,000 g/mol, the zeta potential, the sieving coefficient for albumin, the PVP content of the fiber and the local aqueous ultrafiltration coefficient are determined for the sterilized hollow fiber membrane filters at 5 different positions on the hollow fiber membrane filter. The results are listed in table 1.

Example 3: Comparative Example

The same materials are used as in example 2. A spinning solution consisting of 16 parts by weight polysulfone, 4 parts by weight polyvinylpyrrolidone and 80 parts by weight DMAC is stirred, heated to 50° C. and degassed so as to process it into a homogeneous spin mass. The spin mass is extruded through an annular spinneret with a centrally controlled precipitant consisting of 54% DMAC and 46% water into a strand. The precipitant is conducted inside the hollow strand. The temperature of the annular spinneret is 40° C. The extruded strand is guided through a precipitation chamber, the atmosphere of which is at a relative humidity of 30%. The height of the precipitation gap is 600 mm, a precipitation gap dwell time of 1.35 sec. is set. The strand is introduced into a precipitating bath consisting of water which is temperature-controlled to 68° C. and precipitated into a hollow fiber membrane. The hollow fiber membrane is then routed through rinsing baths which are temperature-controlled to a temperature of 75° C. to 90° C. The hollow fiber membrane thereafter undergoes a drying process between 100° C. and 150° C. The hollow fiber membrane obtained is then taken up on a coiler and formed into a tow. Hollow fiber membrane bundles are produced from the coiled tow. The porosity of the hollow fiber membrane is thereafter determined.

The hollow fiber membrane bundle is further processed into hollow fiber membrane filters using known techniques. The hollow fiber membrane filter obtained is sterilized in the next step according to a method described in the prior art (DE 39 36 785 C1). The sieving coefficient for a dextran at a molecular weight of 10,000 g/mol, the zeta potential, the sieving coefficient for albumin, the PVP content of the fiber and the local ultrafiltrations are determined for the sterilized hollow fiber membrane filters at 5 different positions on the hollow fiber membrane filter. The results are listed in table 1.

TABLE 1

| Ultrafiltration coefficients determined at local positions [ml/h*mmHg] | Example 2: Example embodiment | Example 3: Comparative example |
|---|---|---|
| Pos. 1 | 137 | 119 |
| Pos. 2 | 142 | 152 |
| Pos. 3 | 148 | 154 |
| Pos. 4 | 142 | 160 |
| Pos. 5 | 144 | 150 |
| Difference min/max | 11 | 35 |
| Deviation from maximum value | 7.7% | 21.8% |
| Zeta potential | −7 mV | −10 mV |
| Porosity | 79.7% | 77% |
| Sieving coefficient albumin | 0.06 | 0.07 |
| Sieving coefficient dextran (10000 g/mol) | 0.63 | 0.40 |
| Clearance, sodium | 268 | 260 |
| Clearance, phosphate | 237 | 200 |
| Clearance, vitamin B12 | 169 | 146 |

The invention claimed is:

1. A hollow fiber membrane comprising at least one polysulfone-based material and at least one polyvinylpyrrolidone-based polymer, wherein the hollow fiber membrane has a porosity of 77.5% to 82%, a sieving coefficient for dextran at a molecular weight of 10,000 g/mol of 0.42 to 0.75 when an aqueous dextran solution is passed therethrough, and a sieving coefficient for albumin of less than 0.01 and a zeta potential of −4 mV to −8 mV, and wherein the hollow fiber membrane is sterile, wherein the radius of the nominal pore size distribution exhibits a maximum in the range of from 22 to 26 A (angstrom).

2. The hollow fiber membrane according to claim 1, wherein the hollow fiber membrane has a porosity of 78% to 81%.

3. The hollow fiber membrane according to claim 1, wherein the hollow fiber membrane has a sieving coefficient for dextran at the molecular weight of 10,000 g/mol of 0.45 to 0.75.

4. The hollow fiber membrane according to claim 1, wherein the hollow fiber membrane has a sieving coefficient for albumin of less than 0.005.

5. The hollow fiber membrane according to claim 1, wherein the hollow fiber membrane has a PVP content of 2.5% to 5% by weight.

6. The hollow fiber membrane according to claim 1, wherein the hollow fiber membrane has an XPS analysis-based PVP content of 18% to 27% by weight on the inside.

7. A hollow fiber membrane filter consisting of a cylindrical housing and a plurality of the hollow fiber membrane of claim 1 which are arranged in the interior of the housing and sealed at the ends in a casting compound such that a first chamber encompassing the interior space of the hollow fiber membranes is formed and a second chamber encompassing the space between the hollow fiber membranes is formed, at least one first fluid port for the supplying of a fluid into the fiber interior, at least one first fluid port for the draining of the fluid from the interior of the fiber, wherein the hollow fiber membranes exhibit a uniform separation capability across the cross section of the hollow fiber membrane filter measured by the hollow fiber membranes having ultrafiltration coefficients in different regions of the hollow fiber membrane filter which differ from one another by no more than 20%.

8. The hollow fiber membrane according to claim 1, wherein the hollow fiber membrane has a porosity of from 79% to 80.5%.

9. The hollow fiber membrane according to claim 1, wherein the hollow fiber membrane has a sieving coefficient for dextran at the molecular weight of 10,000 g/mol of 0.55 to 0.7.

10. The hollow fiber membrane according to claim 1, wherein the hollow fiber membrane has a sieving coefficient for dextran at the molecular weight of 10,000 g/mol of 0.6 to 0.7.

11. The hollow fiber membrane according to claim 1, wherein the hollow fiber membrane has a sieving coefficient for albumin of less than 0.001.

12. The hollow fiber membrane according to claim 1, wherein the hollow fiber membrane has a zeta potential of −6 mV to −8 mV.

13. The hollow fiber membrane according to claim 1, wherein the radius of the nominal pore size distribution exhibits a maximum in the range of 23 to 26 Å (angstrom).

14. The hollow fiber membrane filter of claim 7, wherein the fluid is a liquid.

15. The hollow fiber membrane filter of claim 7, wherein the fluid is a gas.

16. The hollow fiber membrane according to claim 1, wherein the sieving coefficient for albumin of less than 0.01 is a plasma sieving coefficient of albumin.

* * * * *